United States Patent [19]

Lubon et al.

[11] Patent Number: 5,831,141

[45] Date of Patent: Nov. 3, 1998

[54] EXPRESSION OF A HETEROLOGOUS POLYPEPTIDE IN MAMMARY TISSUE OF TRANSGENIC NON-HUMAN MAMMALS USING A LONG WHEY ACIDIC PROTEIN PROMOTER

[75] Inventors: Henryk Lubon, Rockville, Md.; William N. Drohan, Springfield, Va.; Lother Hennighausen, Chevy Chase, Md.

[73] Assignees: United States of America as represented by the Department of Health and Human Services, Washington, D.C.; American Red Cross, Rockville, Md.

[21] Appl. No.: 943,246

[22] Filed: Sep. 10, 1992

Related U.S. Application Data

[63] Continuation-in-part of Ser. No. 638,995, Jan. 11, 1991, abandoned.

[51] Int. Cl.⁶ .............................. C12N 5/00; C12N 15/00; C12P 21/06; C12P 21/04
[52] U.S. Cl. .................. 800/2; 800/DIG. 1; 435/69.1; 435/69.6; 435/172.3; 435/320.7; 536/24.1; 935/60
[58] Field of Search .................................. 800/2, DIG. 1; 435/172.3, 69.1, 69.6, 320.1; 536/23.2, 24.1, 25.4; 935/9, 10, 6, 14, 19, 60, 64

[56] References Cited

U.S. PATENT DOCUMENTS

| | | |
|---|---|---|
| 4,775,624 | 10/1988 | Bang et al. . |
| 4,775,642 | 10/1988 | Bang . |
| 4,873,316 | 10/1989 | Meade et al. . |
| 4,959,318 | 9/1990 | Foster . |
| 4,968,626 | 11/1990 | Foster . |
| 4,992,373 | 2/1991 | Bang et al. . |

FOREIGN PATENT DOCUMENTS

| | | |
|---|---|---|
| 0 264 166 | 4/1988 | European Pat. Off. . |
| 0 279 582 | 8/1988 | European Pat. Off. . |
| WO 88/00239 | 1/1988 | WIPO . |
| WO 88/01648 | 3/1988 | WIPO . |
| WO 90/05188 | 5/1990 | WIPO . |
| WO91/08216 | 6/1991 | WIPO . |
| WO 92/11358 | 7/1992 | WIPO . |

OTHER PUBLICATIONS

Bischoff et al. A 17.6 KBP Region Located Upstream of the Rabbit Wap Gene Directs High Level Expression of a Functional Human Protein Variant in Transgenic Mouse Milk, Febs, vol. 305, No. 3, 265–268 (Jul. 1992).
Young et al., "Expression of Human Protein C in the Milk of Transgenic Mice", *J. Cell. Biochem. Suppl.* 154A:174, Abstract No. B 025 (1991).
Biery et al (1988) Theriogenology 29, 224.
Bondioli et al (1991) in Transgenic Animals: proceeding of the Symposium on Transgenic Technology, ed. First et al, pp. 265–273.
Massey (1990) J. Reprod. Fert. Suppl. 41, 199–208.
Hill et al (1992) Theriogenology 37, 222.
Puhler et al (1993) Genetic Engineering of Animals, VCH, Weinheim, Germany, pp. 139–140.
Plutzky et al (1986) Proced. natl. Acad. Sci. 83, 546–550.
Tomaserto et al (1989) Molec. Endo crm. 3, 1579–1584.
Velander et al (1992) Proced. Natl. Acad. Sci. 89, 12003–12007.
Palmiter et al (1986) Ann. Rev. Genet. 20, 465–499.
Denman et al. (Sep. 1991) *Bio/Technology* 9: 839–843, "Transgenic Expression of a Variant of Human tPA in Goat Milk: Purification and Characterization of the Recombinant Enzyme".
Ebert et al. (Sep. 1991) *Bio/Technology* 9: 835–838, "Transgenic Production of a Variant of Human tPA in Goat Milk: Generation of Transgenic Goats and Analysis of Expression".
Gordon et al. (Nov. 1987) *Bio/Technology* 5: 1183–1187, "Production of Human Tissue Plasminogen Activator in Transgenic Mouse Milk".
Krimpenfort et al. (Sep. 1991) *Bio/Technology* 9: 844–847, "Generation of Transgenic Dairy Cattle Using 'In Vitro' Embryo Production".
Walls et al. (1989) *Gene* 81: 139–149, "Amplification of Multicistronic Plasmids in the Human 293 Cell Line and Secretion of Correctly Processed Recombinant Human Protein C".
Wright et al. (Sep. 1991) *Bio/Technology* B: 830, "High Level Expression of Active Human Alpha–1–Antitrypsin in the Milk of Transgenic Sheep".
Van et al. (Jul. 1990) *Bio/Technology*: 8655–661, "Characterization and Novel Purification of Recombinant Human Protein C from Three Mammalian Cell Lines".
Velander et al. (1990) Abstract presented at the 1990 Annual Meeting (Nov. 11–16, 1990) American Institute of Chemical Engineering, "The Expression of Human Protein C in the Milk of Transgenic of the Mice".
Grinnell et al., (19900 "Native and Modified Recobinant Human Protein C and Related Anticoagulants", Chapter 3, Bruley and Drohan, Eds., Portfolio Co., The Woodlands, Texas.
Wydro, R.M. (1990) "Transgenic Production of Protein C" in Protein C and Related Anticoagulants, An International Symposium, Held Feb. 26–27, 1992 in San Diego, CA.

(List continued on next page.)

*Primary Examiner*—Deborah Crouch
*Attorney, Agent, or Firm*—Foley & Lardner

[57] ABSTRACT

Heterologous polypeptides are produced in the milk of transgenic non-human mammals by the expression of a stably integrated DNA sequence containing the long whey acidic protein promoter operably linked to a DNA sequence encoding a heterologous polypeptide and a signal sequence. The transgenic non-human mammals of the present invention are produced by introducing this DNA sequence such that the DNA sequence is stably integrated into the DNA of germ line cells of the mature mammal and inherited in normal Mendelian fashion. A representative heterologous polypeptide is protein C.

20 Claims, 8 Drawing Sheets

OTHER PUBLICATIONS

Hogan et al. (1981), Manipulating the Mouse Embryo, Cold Spring Harbor laboratory, New York, pp. 155–203.

Grinnell et al. (1987) *Biotechnology* 5: 1189–1192 "Trans-activated expression of fully gamma–carboxylated recombinant human protein C, an antithrombotic factor".

Pittius et al. (1988), *Proc. Natl. Acad. Sci., U.S.A.* 85: 5874–5878, "A milk protein gene promoter directs the expression of human tissue plasminogen activaator cDNA to the mammary gland in transgenic mice".

Colpan et al. (1984) *J. Chromatography* 296: 339–353 "HPLC of high–molecular–weight nucleic acids on the macroporous ion exchanger, nucleogen".

Clark et al (Jan., 1987) *TIBTECH* 5: 20–24 "Pharmaceuticals from transgenic livestock".

Campbell et al. (1984) *Nucleic Acids Research* 12: 8686–8697 "Comparsion of the whey acid protein genes of the rat and mouse".

Brinster et al (1988) Proced. Natl. Acads. Sci. 85, 836–840.

Hennighausen (1990) Protein Expression and Purification 1, 3–8.

Genetic Engineering News, Oct. 15, 1995, pp. 8–9.

HUMAN PC cDNA WITH WAP PRO AND GENE

WAP-ProC PRIMER PAIRS

| PRIMER PAIRS | FRAGMENT LENGTH |
| --- | --- |
| a - c | 441 |
| b - c | 324 |
| b - d | 563 |
| a - e (ENDOGENOUS) | 222 |

OTHER PRIMER PAIRS

| | |
| --- | --- |
| 18S rRNA | 337 |
| MOUSE LDH | 331 |
| PIG UPA | 319 |

MAPPING OF CALCIUM DEPENDENT CONFORMER BY METAL-DEPENDENT IMMUNOAFFINITY INTERACTION

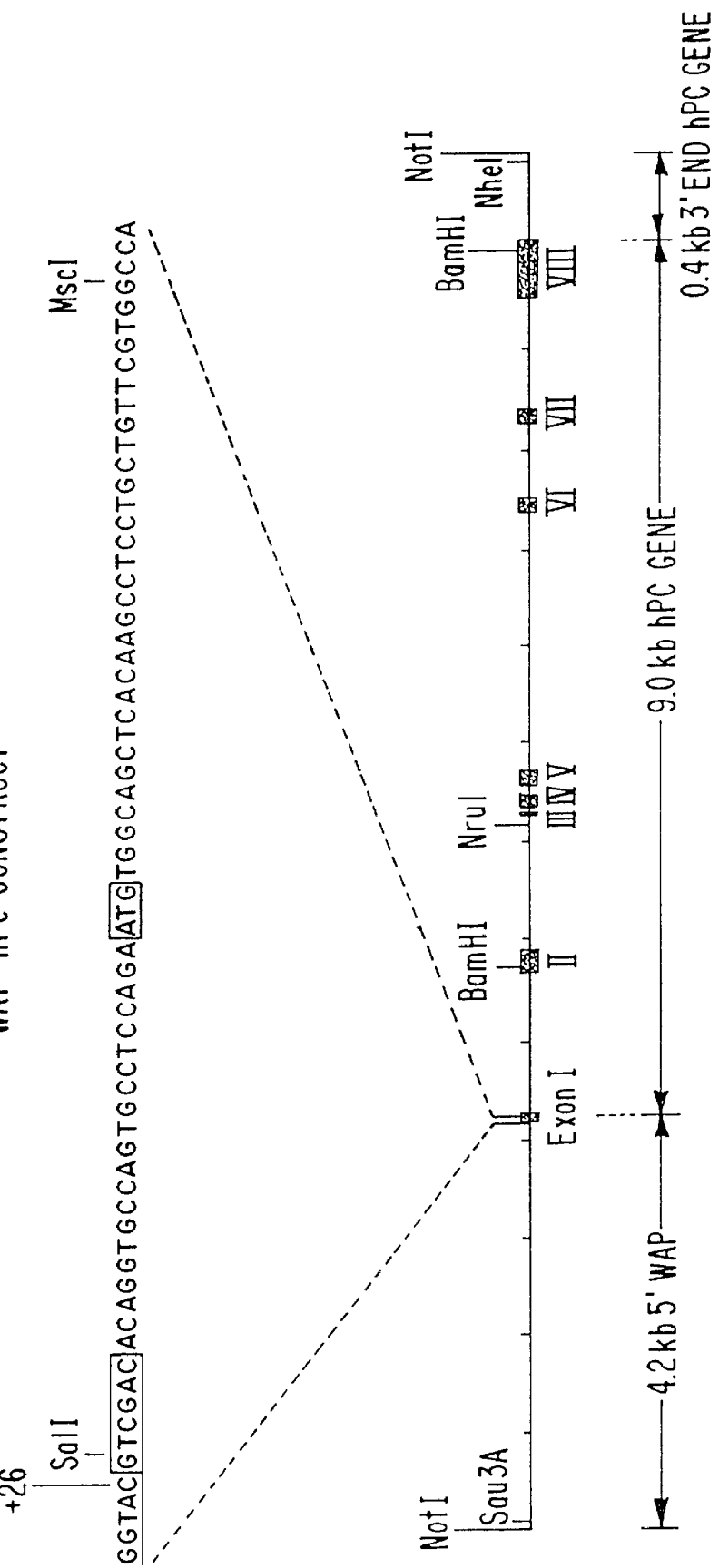

EXPRESSION OF A HETEROLOGOUS POLYPEPTIDE IN MAMMARY TISSUE OF TRANSGENIC NON-HUMAN MAMMALS USING A LONG WHEY ACIDIC PROTEIN PROMOTER

This application is a continuation-in-part of U.S. Ser. No. 07/638,995, filed Jan. 11, 1992, which is herein incorporated by reference.

The present invention relates to the production of natural and modified forms of the human coagulation factor protein C. In particular, the invention relates to a transgenic animal containing, stably incorporated in its genomic DNA, an exogenous gene which is expressed specifically in mammary tissue, such that protein C is secreted into milk produced by the animal. In particular, the invention relates to the production of natural and modified forms of protein C in the milk of a transgenic non-human mammal using a DNA molecule that comprises a long whey acidic protein promoter fragment and genomic DNA encoding human protein C. The long whey acidic protein promoter fragment also can be used to express high levels of other genes in mammary cells of transgenic non-human mammals.

BACKGROUND OF THE INVENTION

Protein C is an important component of the coagulation system that has strong anticoagulant activity. In its active form it is a serine protease that proteolytically inactivates Factors $V_a$ and $VIII_a$.

Human protein C (hPC) is a 62 kD, disulfide-linked heterodimer consisting of a 25 kD light chain and a 41 kD heavy chain which circulates as an inactive zymogen in plasma. At the endothelial cell surface it is activated to activated protein C (APC) by limited thrombin proteolysis in the presence of thrombomodulin; cleavage of an Arg-Leu bond in the amino terminal portion of the heavy cain releases a 12 amino acid peptide. See generally Gardiner & Griffin in *PROGRESS IN HEMATOLOGY*, Vol. XIII at page 265–278 (Brown, Grune and Stratton, Inc. 1983).

Several regions of the molecule have important implications for function as an anticoagulant in the regulation of hemostasis. The amino terminal portion of the light chain contains the nine γ-carboxyglutamic acid (Gla) residues required for calcium-dependent membrane binding and functional activation. Another post-translational modification is β-hydroxylation of aspartic acid reside 71, possibly required for calcium-dependent membrane binding which is independent of the binding activity of the Gla regions.

There are a variety of clinical situations for which protein C may prove beneficial. It may serve as replacement therapy in homozygous deficient infants suffering from purpura fulminans neonatalis. Other conditions include patients with a previous history of warfarin-induced skin necrosis who must have additional warfarin therapy, heparin-induced thrombocytopenia, septic shock for prevention of intravascular coagulation and organ damage, and for fibrinolytic therapy, as protein C can protect tPA from plasma inhibitor proteins. Table 1 represents one estimate of the number of individual cases of several clinical syndromes which might be treated by purified protein C. Because there has not been sufficient material available from plasma for clinical trials until recently, these data are necessarily based on an incomplete assessment of the therapeutic potential for protein C.

TABLE 1

PARTIAL ESTIMATE OF U.S. CLINICAL REQUIREMENTS FOR PROTEIN C AND ACTIVATED PROTEIN C

| Indication | Estinated Dose (mg) Per Treatment | # Treatments Per Year | Total U.S. Req. (Kg) |
|---|---|---|---|
| Septic Shock | 5–50 | 120,000 | 0.6–6.0 |
| Thrombolytic Therapy** | 10–100 | 800,000 | 8–80 |
| Hip Replacement | 10–100 | 200,000 | 2–20 |
| Homozygous Deficient | 3 | 100 × 365* | 0.10 |
| Heterozygous Deficient | 50 | 1,000 | 0.05 |
| Total | | | 10.8–106.2 |

*100 individuals in U.S. × 365 treatment/year
**Refers to the use of APC, following thrombolytic therapy, to prevent the reformation of blood clots.

The gene for human protein C has been cloned and sequenced, as has bovine protein C gene. See Forster et al., *Proc. Nat'l Acad. Sci. USA* 82: 4673 (1985); U.S. Pat. No. 4,775,624. It is synthesized as an inactive precursor that undergoes several proteolytic events during the processes of secretion and activation. First, a signal sequence as proteolytically removed upon secretion. A second proteolytic event removes the dipeptide lys156 arg157, producing the inactive zymogen, a two chain disulfide bridged protein, consisting of a light chain of 155 amino acids and a heavy chain of 262 amino acids. The zymogen is activated by a final proteolytic event that removes residues 158–169, yielding active protein C, a serine protease with potent anticoagulant activity. Beckmann et al., *Nucleic Acids Res.* 13: 5233 (1985).

In addition to proteolytic processing, human protein C undergoes several post-translation modifications. Perhaps most salient among these modifications is the γ-carboxylation of the first nine glutamic acid residues in protein C, by a vitamin K dependent enzyme. DiScipio & Davie, *Biochemistry* 18: 899 (1979). Gamma-carboxylation is required for anticoagulant activity, and is associated with $Ca^{2+}$-dependent membrane binding. The anticoagulant activity of protein C varies directly with the extent of γ-carboxylation, and the highest levels of activity are achieved only when γ-carboxylation of the sixth and seventh glutamic acid residues is effected. Zhang & Castellino, *Biochemistry* 29: 10829 (1990).

Protein C is also post-translationally modified by β-hydroxylation of aspartic acid 71. Drakenberg et al., *Proc. Nat'l Acad. Sci. USA* 80: 1802 (1983). Beta-hydroxylation may be important to protein C activity. Although its function is not known it has been suggested that it may be involved in γ-carboxyglutamic acid independent $Ca^{2+}$ binding, and it may be required for full anti-coagulant activity.

Human protein C is also glycosylated. Kisiel, *J. Clin. Invest.* 64: 761 (1979). It contains four potential N-linked glycosylation sites, located at Asn97, Asn248, Asn313 and Asn329. The first three signals match the consensus Asn-X-Ser/Thr glycosylation sequences, and are actively glycosylated. There is an atypical glycosylation signal at Asn329, Asn-X-Cys-Ser. The Asn329 signal is glycosylated in bovine protein C, but it is not yet known if Asn329 is glycosylated in human protein C. Miletich et al., *J. Biol. Chem.* 265: 11397 (1990). The pattern and extent of glycosylation can alter the physiological activity of protein C.

Until recently, human protein C for experimental and therapeutic use was obtained exclusively from human plasma. Unfortunately, the quantity of protein that can be obtained from human serum is limited. Furthermore, products derived from human serum pose difficulties of reliability, purity and safety.

The expression of therapeutic proteins by recombinant DNA technology is an attractive alternative to plasma production of protein C, in that it eliminates the risk of potential contamination with blood-borne viruses and theoretically provides an unlimited supply of product. But the complexity of the post-translational modifications, as discussed above, has rendered problematic the production of commercially useable amounts of suitably active protein C by expression in a heterologous host.

In fact, it has not been possible to produce vitamin K-dependent proteins like protein C at sufficiently high levels in an active form, despite efforts to do so using a variety of expression systems. See Grinnell et al. in Volume 11 of ADVANCES IN APPLIED BIOTECHNOLOGY SERIES, Chapter 3 (Gulf Publishing Co.). In particular, any prospect for expressing protein C in mammary glands of a transgenic animal and secreting the protein into milk, see, e.g., U.S. Pat. No. 4,873,316 (1989), is clouded by the fact that protein C is normally synthesized in the liver. Even HepG2 cell lines derived from human liver produce aberrant forms of protein C. Marlar & Fair (1985).

In this regard, it has been observed that a mouse mammary epithelial cell line (C-127) transfected with a bovine papilloma virus (BPV) vector bearing the cDNA for human protein C expressed protein C that was only 30–40% active. Further analysis revealed that the protein C contained diminished levels of $\gamma$-carboxyglutamic acid and little, if any, $\beta$-hydroxyaspartic acid. Suttie et al., *Thrombosis Res.* 44: 129 (1986). These experiments indicate that mouse mammary epithelial cells cannot perform all of the post-translational modifications necessary for obtaining suitably active protein C, which in turn casts doubt on the likelihood of obtaining such protein C from the milk of a transgenic mammal.

SUMMARY OF THE INVENTION

It is therefore an object of the present invention to provide a transgenic animal which produces in its milk recombinant protein C that comprises a significantly higher percentage of active protein than has been achieved heretofore.

It is another object of the present invention to provide a process for producing protein C in commercially useable amounts, by means of a transgenic mammal.

In accomplishing the foregoing objects, there has been provided, in accordance with one aspect of the present invention, a transgenic mammal containing an exogenous DNA sequence stably integrated in its genome, wherein the exogenous DNA sequence comprises a promoter operably linked to a DNA sequence encoding a polypeptide having protein C activity and a signal peptide, wherein the promoter is specifically active in mammary cells, particularly mammary epithelial cells, and the signal peptide is effective in directing the secretion of the protein C into the milk of the transgenic mammal.

In a preferred embodiment, the promoter is a whey acidic protein promoter. In a highly preferred embodiment the promoter comprises substantially the 5' 4.2 kb Sau3A-Kpn1 promoter fragment of the mouse whey acidic protein gene, or a variant thereof.

In another aspect in a preferred embodiment the DNA sequence encoding a polypeptide having human protein C activity comprises portions of the non-coding regions of the human protein C gene. In a particularly preferred embodiment of this type the DNA sequence gene comprises substantially the human protein C gene from 21 basepairs upstream of the protein C start codon to the NheI site in the 3' end of the protein C gene, or a variant thereof is among the most highly preferred.

In a particularly preferred embodiment, the exogenous DNA sequence comprises a DNA sequence consisting essentially of the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene.

In accordance with another aspect of the present invention, there has been provided a process for the production of protein C, comprising the steps of (A) providing a transgenic mammal characterized by an exogenous DNA sequence stably integrated in its genome, wherein the exogenous DNA sequence comprises a promoter operably linked to a DNA sequence encoding a polypeptide having protein C activity and a signal peptide, the promoter being specifically active in mammary cells and the signal peptide being effective in directing the secretion of the protein C into the milk of the transgenic mammal; (B) producing milk from the transgenic mammal; (C) collecting the milk; and (D) isolating the polypeptide from the milk.

In a highly preferred embodiment of this aspect of the invention, the promoter comprises substantially the 5' 4.2 kb Sau3A-Kpn1 promoter fragment of the mouse whey acidic protein gene, or a variant thereof.

Additionally, in a preferred embodiment the DNA sequence encoding a polypeptide having human protein C activity comprises portions of the non-coding regions of the human protein C gene. In a particularly preferred embodiment of this type the DNA sequence gene comprises substantially the human protein C gene from 21 basepairs upstream of the protein C start codon to the NheI site in the 3' end of the protein C gene, or a variant thereof is among the most highly preferred.

In addition, is certain a particularly preferred embodiment, the exogenous DNA sequence comprises a DNA sequence consisting essentially of the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene.

In accordance with still another aspect of the present invention, a process has been provided for producing transgenic animals, comprising the steps of (A) providing a mixture containing a genetic construct; (B) subjecting the mixture to anion-exchange high performance liquid chromatography to obtain purified genetic construct; and thereafter (C) microinjecting an aqueous buffer solution containing the purified genetic construct into an animal embryo. In a preferred embodiment, step (B) comprises applying the mixture to an anion-exchange high performance liquid chromatography column, eluting the genetic construct from the column, and then subjecting the genetic construct to a second anion-exchange high performance liquid chromatography.

In a preferred embodiment of this aspect of the invention, the double-stranded DNA is selected from the group consisting of a double-stranded DNA comprising substantially the 5' 4.2 kb Sau3A-Kpn1 promoter fragment of the mouse whey acidic protein promoter, a double-stranded DNA comprising substantially a fragment of the human protein c gene beginning 21 basepairs upstream of the protein C start codon and ending at the NheI site in the 3' end of the protein C gene, and a double-stranded DNA comprising a DNA sequence consisting essentially of the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene.

In accordance with yet another aspect of the invention, there has been provided a process for the production of a polypeptide in the milk of a transgenic non-human mammal, comprising the steps of providing a non-human transgenic mammal characterized by an exogenous DNA sequence stably integrated in its genome, wherein said exogenous DNA sequence comprises substantially the 5' 4.2 kb Sau3A - Kpn1 promoter of the mouse whey acidic protein gene, or a variant thereof, operably linked to a DNA sequence encoding said polypeptide and a signal peptide, said promoter being specifically active in mammary cells and said signal peptide being effective in directing the secretion of said polypeptide into the milk of said transgenic mammal; producing milk from said transgenic mammal; collecting said milk; and isolating said polypeptide from said milk. In a particularly preferred embodiment of this aspect of the invention, the exogenous DNA sequence comprises the 5' 4.2 kb Sau3A - Kpn1 promoter fragment of the mouse whey acidic protein promoter.

The accordance with yet another aspect of the invention there has been provided a transgenic non-human mammal containing an exogenous DNA sequence stably integrated in its genome, wherein the exogenous DNA sequence comprises substantially the 4.2 kb Sau3A-Kpn1 whey acidic protein promoter fragment, or a variant thereof, operably linked to a DNA encoding a polypeptide whereby the protein is expressed specifically in mammary cells of the transgenic mammal and the protein comprises a signal peptide, the peptide being effective in directing the secretion of the protein into the milk of said mammal. In a particularly preferred embodiment of this aspect of the invention, the exogenous DNA sequence comprises the 5' 4.2 kb Sau3A-Kpn1 promoter fragment of the mouse whey acidic protein promoter.

In certain preferred embodiments of various aspects of the invention, the transgenic mammal is mouse, rabbit, pig, sheep or goat. In some most highly preferred embodiments the animal is pig or sheep.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 6 is a schematic diagram representing a highly preferred murine WAP—human protein C construct. In this construct, a 4.2 kb 5' murine whey acidic protein promoter fragment is linked to a 9.4 kb genomic fragment encoding human protein C which includes the 400 bp extending from the end of exon VIII to the NheI site in the 3' end of the human protein C gene. The sequence of the WAP-hPC junction (SEQ ID NO:1) is shown above the schematic diagram.

DETAILED DESCRIPTION OF THE INVENTION

Figure 1:
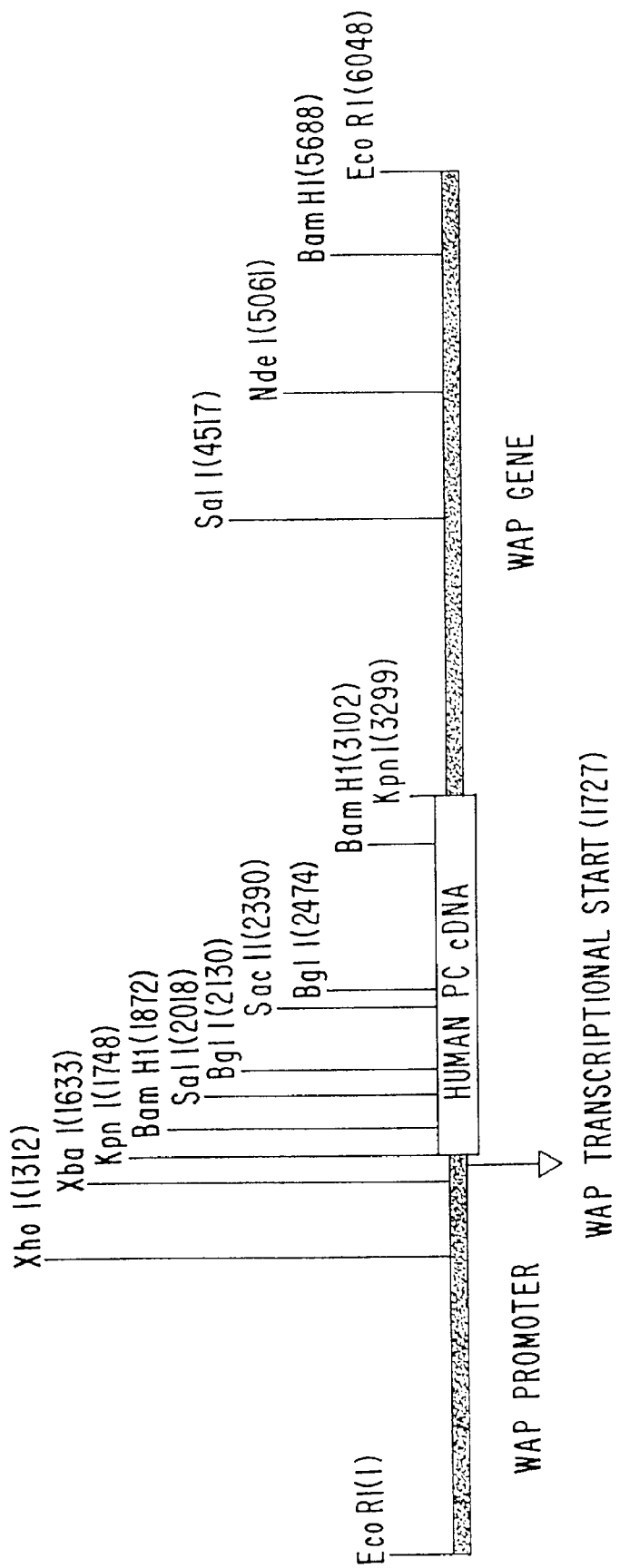
FIG. 1 is a schematic diagram representing WAPpCI, a construct which contains cDNA encoding human protein C inserted into an intact murine whey acidic protein (WAP) gene at the unique Kpn1 site.

Notwithstanding past failures to express recombinant protein C with suitably high activity in several different expression systems, including transformed mammary cells, it has been discovered that recombinant protein C characterized by a high percentage of active protein can be obtained in the milk of transgenic animals that incorporate DNAs according to the present invention. Transgenic animals of the present invention are produced by introducing into developing embryos DNA that encodes protein C, such that the DNA is stably incorporated in the DNA of germ line cells of the mature animal and inherited in normal, mendelian fashion.

In accordance with the invention, DNAs can be introduced into embryos by a variety of means to produce transgenic animals. For instance, totipotent or pluripotent stem cells can be transformed by microinjection, calcium phosphate mediated precipitation, liposome fusion, retroviral infection or by other means. The transformed cells can then be introduced into embryos and incorporated therein to form transgenic animals. In a preferred method, developing embryos can be infected with retroviral vectors and transgenic animals can be formed from the infected embryos. In the most preferred method, however, the DNAs of the invention are injected into embryos, preferably at the single-cell stage, which are allowed to develop into mature transgenic animals.

Suitable protein C-encoding DNA used for producing transgenic animals in this fashion can be obtained using human liver tissue as a source for cloning the hPC gene. The DNA coding for protein C can be fused, in proper reading frame, with appropriate regulatory signals, as described in greater detail below, to produce a genetic construct which is then amplified, for example, by propagation in a bacterial vector, according to conventional practice.

The amplified construct is thereafter excised from the vector and purified for use in microinjection. The purification is preferably accomplished by means of high performance liquid chromatography (HPLC), which rids the construct of contamination from the bacterial vector and from polysaccharides typically present when other techniques, such as conventional agarose electroelution, are used. The preferred HPLC method entails sorbing the construct onto an anion-exchange HPLC support and selectively eluting the construct from the support, preferably with an aqueous sodium chloride solution, thereby to eliminate contamination from the vector. (Elution may be effected by other means, such as a pH gradient.) Alternatively but less preferably, the excised construct can be purified by ultracentrifugation through an aqueous sucrose gradient.

Since it is preferable that the construct have the minimum amount of impurities, more than one cycle of HPLC or other purification is advantageous. In particular, the use of HPLC-purified DNA for microinjection, as described above, allows for remarkably high transformation frequencies, on the order of 20% or more in both mice and pigs.

All lactating animals, that is, all mammals, are suitable for use according to the present invention. Preferred mammals include mice, rats, rabbits, pigs, sheep, goats and cows. More particularly, mice, pigs, sheep and cows are preferred. Most preferred at present are mice, pigs and sheep.

DNA constructs useful in the present invention provide a DNA sequence encoding protein C operably linked to all the cis-acting signals necessary for mammary tissue specific expression of protein C, post-translational modification of protein C, secretion of protein C into milk, and full biological activity of protein C.

DNAs useful in the invention include genomic or complementary DNAs that encode naturally occurring protein C. In a preferred embodiment DNAs encoding human protein C are employed, including cDNA and genomic DNAs. DNAs encoding protein C from other species may also be used, such as the protein C encoded by rats, pigs, sheep, cows and chimpanzees.

In a particularly preferred embodiment, human genomic DNAs encoding protein C are employed. Among the most highly preferred human genomic DNAs is the fragment of the human protein C gene beginning 21 basepairs upstream of the protein C start codon and ending at the NheI site in the 3' end of the protein C gene. This fragment, approximately 9.4 kb long, contains regulatory elements that engender high expression of human protein C in the milk of non-human transgenic mammals. Some of these regulatory elements are the AUG start codon, donor and acceptor splice signals, the secretion peptide, and the translation termination, transcription termination and polyadenylation signals.

It will be appreciated that there may be additional regulatory elements in the fragment that aid the production of transgenic non-human mammals that express high levels of protein C in their milk. Some of these signals may be transcription or translation control signals, or those associated with transport out of the cell. Other signals may play a role in efficient chromosomal integration or stability of the integrated DNA. Various regions of the fragment may contain such signals, such as the region between the end of exon VIII and the NheI site in the 3' end of the protein C gene.

It will be readily appreciated that deletional and other mutational techniques may be employed to elucidate further all the signals in this fragment that confer high levels of protein C expression in the milk of transgenic animals.

It will also be appreciated that the 9.4 kb protein C fragment described above can be modified using recombinant DNA techniques in an almost infinite number ways. 3' or 5' portions of the protein C gene can be added, or a few bases at either end may be removed. Introns can be removed or added. Portions of one or more introns can be deleted. Additional DNA can be inserted into them. The sequences of the introns can be altered. Exons can be modified in accordance with the discussion of modified protein C molecules set forth below. Most such modified forms of the preferred genomic protein C fragment will not be significantly changed in their ability in transgenic animals to engender the production of milk-born protein C. Thus, these substantially similar fragments will be equivalent in the invention to the particularly disclosed 9.4 kb fragment of human protein C that begins 21 basepairs upstream of the protein C start codon and ends at the NheI site in the 3' end of the protein C gene.

Modified protein C sequences also can be employed in the present invention. Useful modifications in this context include but are not limited to those that alter the post-translational processing of protein C, that alter the size of protein C, that fuse protein C or portions thereof to portions of another protein, or that alter the active site of protein C. Preferred modifications include those that provide an activated protein C and those that provide for activation of protein C in the absence of thrombomodulin. In a preferred embodiment, modified forms of human protein C are employed.

Such modifications can be introduced into protein C by techniques well known to the art, such as the synthesis of modified genes by ligation of overlapping oligonucleotide, and by introducing mutations directly into cloned genes, as by oligonucleotide mediated mutagenesis, inter alia.

The cis-acting regulatory regions useful in the invention include the promoter used to drive expression of the protein C gene. Promoters useful in the invention are active in mammary tissue. Particularly useful are promoters that are specifically active in mammary tissue, i.e., are more active in mammary tissue than in other tissues under physiological conditions where milk is synthesized. Most preferred are promoters that are both specific to and efficient in mammary tissue. By "efficient" it is meant that the promoters are strong promoters in mammary tissue that can support the synthesis of large amounts of protein for secretion into milk.

Among such promoters, the casein, lactalbumin and lactoglobulin promoters are preferred, including, but not limited to the α-, β- and γ-casein promoters and the a-lactalbumin and γ-lactoglobulin promoters. Preferred among the promoters are those from rodent (murine and rat), pigs and sheep, especially the rat β-casein promoter and the sheep β-lactoglobulin promoter. The most preferred promoters are those that regulate a whey acidic protein (WAP) gene, and the most preferred WAP promoter is the murine WAP promoter.

A most highly preferred promoter is the 4.2 kb Sau3A-Kpn1 promoter fragment of the mouse whey acidic protein promoter. It has been found that this fragment is highly efficacious in directing the production of high levels of a protein in the milk of a transgenic animal. In the case of human protein C this mouse whey acidic protein promoter fragment has engendered the production of active protein C in the milk of transgenic animals in concentrations above 4 mg/ml (by polyclonal ELISA).

It will be readily appreciated, as for the 9.4 kb protein C genomic DNA discussed above, the 4.2 kb Sau3A-Kpn1 whey acidic protein promoter fragment can be modified by recombinant DNA techniques readily available to those of ordinary skill in the art. Thus, the fragment can be shortened, keeping in mind that the 2.4 kb 5' WAP promoter fragment gives rise to very much lower yields. It can be lengthened to include more of the whey acid protein promoter region or other portions of the whey acid protein gene. Portions can be removed, and DNA can be inserted into the fragment. Internal bases can be altered. In the majority of cases these alternatives will not affect the ability of this promoter fragment to induce very high levels of expression. Fragments modified in this way, giving the expected high yields of protein in transgenic milk, are substantially similar variants of the 4.2 kb 5' promoter fragment. They also are useful in the present invention and are functionally equivalent in this respect to the 4.2 kb Sau3A -Kpn1 whey acidic protein promoter fragment itself.

Also important to the invention are the signal sequences that direct secretion of protein into the milk of the transgenic animal. In this regard, both endogenous and heterologous signal sequences are useful in the invention. Generally, the signal peptides of proteins normally secreted into milk are useful in the invention. The signal sequences of proteins that occur in high concentration in milk are particularly preferred, such as the signal peptides of the caseins, lactalbumins and lactoglobulins, including, but not limited to the signal peptides of the α-, β- and γ-caseins and a-lactalbumin and β-lactoglobulin. More particularly, the signal sequence of whey acidic protein is preferred, most particularly the signal sequence of the murine whey acidic protein.

Also particularly preferred are the signal peptides of secreted coagulation factors. Especially preferred in this regard are the signal peptides of protein C, and t-PA. Most especially preferred is the secretion signal of human protein C.

Among the sequences that regulate transcription that are useful in the invention, in addition to the promoter sequences discussed above, are enhancers, splice signals, transcription termination signals and polyadenylation sites, among others. Particularly useful regulatory sequences increase the efficiency of mammary cell specific expression of protein C in transgenic animals.

Especially useful in this regard are the other transcription regulatory sequences of genes expressed at high levels in mammary cells, such as the α-, β- and γ-casein genes and the α-lactalbumin and β-lactoglobulin genes mentioned above. Preferred sources for regulatory sequences in this regard are rodents (mice and rats), pigs and sheep.

Exemplary of preferred regulatory sequences are those associated with the rat β-casein gene and the sheep β-lactoglobulin gene, respectively. The regulatory sequences most preferred for use in the present invention are those associated with whey acidic protein genes. Particularly preferred in this context are regulatory sequences of the murine whey acidic protein.

Among the sequences that regulate translation, in addition to the signal sequences discussed above, are ribosome binding sites and sequences that augment the stability the protein C mRNA. Especially useful are the translation regulatory sequences of genes expressed at high levels in mammary cells. For instance, the regulatory sequences of the α-, β- and γ-casein genes and the a-lactalbumin and β-lactoglobulin genes are preferred, especially those from rodents (mice and rats), pigs and sheep. Even more particularly preferred are the regulatory sequences of rat β-casein and the sheep β-lactoglobulin genes.

The most preferred translational regulatory sequences of the invention are those of the whey acidic protein and the protein C genes. And the most particularly preferred regulatory sequences are those of the murine whey acidic protein and human protein C, including human genomic protein C and human protein C CDNA constructs, and including human protein C cDNA constructs that contain intron sequences. Among these, the most highly preferred are the regulatory sequences of the human protein C gene in the region beginning 21 basepairs upstream of the protein C start codon and ending at the NheI site in the 3' end of the protein C gene, and the regulatory sequences of the mouse whey acidic protein promoter in the 5' 4.2 kb Sau3A-Kpn1 promoter fragment of the mouse whey acidic protein promoter, most particularly when they are used together.

Especially useful in the present invention are sequences that advantageously modulate post-translational modifications of protein C, such that the protein C produced in the transgenic animals of the invention is active. In particular, the genomic sequences of the human protein C gene are preferred.

Thus, in accordance with the present invention a DNA sequence that encodes protein C is operably linked to cis-acting regulatory sequences which allow for efficient expression of protein C in milk. The resulting chimeric DNA is introduced into a mammalian embryo, where it integrates into the embryonic genome and becomes part of the heritable genetic endowment of all the cells, including the germ line cells, of the adult which develops from the embryo. The protein C which is expressed in the mammary tissue and secreted into the milk of a transgenic mammal obtained in this manner displays a surprisingly high percentage of active protein, as measured by enzymatic and coagulation-inhibition assays which are conventionally employed to detect protein C activity, such as ELISAs, chromogenic activity assays and coagulation inhibition assays. Levels of active protein on the order of 80% to 90% or more are characteristic of the protein C expressed in accordance with the present invention.

Obtaining milk from a transgenic animal within the present invention is accomplished by conventional means. McBurney et al., *J. Lab. Clin. Med.* 64: 485 (1964). The protein C contained in such milk can be purified by known means without unduly affecting activity. One suitable approach to purification in this regard is immunoaffinity chromatography. Alternatively, the expressed protein C can be isolated from the milk by other conventional means, for instance, by the method of Kisiel, *J. Clin. Invest.* 64: 761 (1979). In any event, it is preferred that protein C produced in milk pursuant to the present invention should be isolated as soon as possible after the milk is obtained from the transgenic mammal, thereby to mitigate any deleterious effect(s) on the stability of the protein.

The present invention is further described by reference to the following, illustrative examples.

EXAMPLE 1

DNAs Useful for Expressing Protein C in Transgenic Animals

The entire murine WAP gene including 2.5 kb of 5' untranslated sequence and 3' untranslated regions was cloned by standard methods. See Campbell et al., *Nucleic Acids Res.* 12: 8685 (1984). The human placental cDNA for human protein C was obtained from C. Shoemacker. Human genomic DNAs encoding protein C were cloned by standard methods from a human placental genomic library. The 9.4 kb fragment was assembled from two genomic clones and a SalI, MseI ended 60 bp synthetic oligonucleotide that was added to the 5' end of the gene.

Standard recombinant DNA techniques were employed to generate the vectors and expression constructs of the preferred embodiments, and for other manipulations of DNA, as set forth below. See Sambrook et al., MOLECULAR CLONING, A LABORATORY MANUAL, Vol. 1–3 (Cold Spring Harbor Press 1989).

(1) WAPpC1

A DNA construct called WAPpC1 was made, consisting of the entire murine WAP gene containing one copy of human protein C cDNA inserted at the unique KpnI site, 24 base pairs 3' of the transcriptional start site of the WAP gene (FIG. 1). This WAP—protein C construct was ligated into a bluescribe vector (Stratagene) to facilitate further manipulation.

(2) WAPpC2

WAPpC2 is similar to WAPpC1, comprising the entire murine WAP gene and human protein C cDNA but differs from WAPpC1 in lacking artefactual 5' flanking sequences present in WAPpC1 as a result of cloning procedures used to make that construct. Specifically, 33 bp 5' to the protein C ATG and 118 "A's" at the 3' end of the protein C cDNA were removed by PCR, and new KpnI sites were added at the 5' and 3' ends.

EXAMPLE 2

Preparation of DNAs for Microinjection

DNA for microinjection was prepared according to the procedures described below for DNA from WAPpC1.

The 9 kb WAPpC1 fragment was removed from the vector with the restriction enzyme EcoRI. After digestion with EcoRI the solution containing the WAPpC1 DNA was brought to 10 mM magnesium, 20 mM EDTA and 0.1% SDS and then extracted with phenol/chloroform. DNA was precipitated from the aqueous layer with 2.5 volumes of ethanol in the presence of 0.3 M sodium acetate at −20° C. overnight. After centrifugation, the pellet was washed with 70% ethanol, dried, and resuspended in sterile distilled water.

DNA for microinjection was purified by HPLC. The digested DNA was precipitated with isopropanol and then dissolved in TE buffer at 0.3 μg/ml. Fragments were purified by HPLC using a Waters GEN FAX PAC HPLC column. The column was run isocratically using a buffer consisting of 25 mM Tris-HCl (pH 7.5), 1 mM sodium EDTA, and 0.63M NaCl. This is the minimum NaCl concentration that will elute the large construct fragment and results in the best resolution from the smaller vector fragment which elutes just prior to the construct fragment. About 15 μg of digested DNA was loaded on the column at a time. The construct-fragment samples from all of the chromatographic runs were then pooled, reprecipitated, and run through the column a second time. Results reported below, for both pigs and mice, were generated using HPLC-purified DNA.

DNA concentrations were determined by agarose gel electrophoresis by staining with ethidium bromide and comparing the fluorescent intensity of an aliquot of the DNA with the intensity of standards. Samples were then adjusted to 10 μg/ml and stored at −20° C., prior to microinjection.

EXAMPLE 3

Transgenic Animals (1) Mice

Transgenic mice were produced essentially as described by Hogan et al., MANIPULATING THE MOUSE EMBRYO (Cold Spring Harbor Press 1986). The procedures employed are outlined below.

Glass needles for micro-injection were prepared using a micropipet puller and microforge. Injections were performed using a Nikon microscope having Hoffman Modulation Contrast optics, with Narashigi micromanipulators and a pico-injector driven by $N_2$ (Narashigi).

Fertilized mouse embryos were surgically removed from the oviducts of superovulated female CD-1 mice and placed into M2 medium. Cumulus cells were removed from the embryos with hyaluronidase at 300 μg/ml. The embryos were then rinsed in new M2 medium, and transferred into M16 medium for storage at 37° C. prior to injection.

After injecting the DNA solution into the male pronucleus, embryos were implanted into avertin-anesthetized CD-1 recipient females made pseudo-pregnant by mating with vasectomized males. Embryos were allowed to come to term and the newborn mice were analyzed for the presence of the transgene as described below.

(2) Pigs

Embryos were recovered from the oviduct. They were placed into a 1.5 ml microfuge tube containing approximately 0.5 ml embryo transfer media (phosphate buffered saline +10% fetal calf serum, Gibco BRL). These were then centrifuged for 12 minutes at 16,000×g RCF (13,450 RPM) in a microcentrifuge (Allied Instruments, model 235C). Embryos were removed from the microfuge tube with a drawn and polished Pasteur pipette and placed into a 35 mm petri dish for examination. If the cytoplasm was still opaque with lipid such that pronuclei are not visible, the embryos were centrifuged again for 15 minutes. Embryos to be microinjected were placed into a microdrop of media (approximately 100 μl) in the center of the lid of a 100 mm petri dish. Silicone oil was used to cover the microdrop and fill the lid to prevent media from evaporating. The petri dish lid containing the embryos was set onto an inverted microscope (Carl Zeiss) equipped with both a heated stage and Hoffman Modulation Contrast optics (200×final magnification). A finely drawn (Kopf Vertical Pipette Puller, model 720) and polished (Narishige microforge, model MF-35) micropipette was used to stabilize the embryos while about 1–2 picoliters of HPLC-purified DNA solution containing approximately 200–500 copies of DNA construct was delivered into the male pronucleus with another finely drawn micropipette. Embryos surviving the microinjection process as judged by morphological observation were loaded into a polypropylene tube (2 mm ID) for transfer into the recipient pig.

(3) Other Animals

Methods for microinjection of other animal species are similar to the methods set forth above.

EXAMPLE 4

Assessment via PCR of WAP/hPC Constructs in Transgenic Animals (1) Preparation of DNA form Transgenic Animals DNA can be prepared from tissue of a transgenic animal of any species by the method exemplified below for mice.

A 5 mm piece of mouse tail was removed from young, potentially transgenic mice at weaning (3 weeks of age), minced, and treated with proteinase K and SDS at 37° C. overnight. The mixture was then incubated with DNase-free RNase at 37° C. for 1–2 hours. DNA was precipitated from the mixture with sodium acetate and ethanol at −20° C. overnight, collected by centrifugation, washed in 70% ethanol and dried. The dried DNA pellet was used directly for PCR. In some cases the mixture was extracted extensively with phenol/chloroform prior to ethanol precipitation.

Essentially the same technique was used to prepare DNA from pigs, and the same or similar techniques can be used to prepare DNA from other animals.

(2) Oligonucleotide Probes used in the PCR Assay

Figure 2:
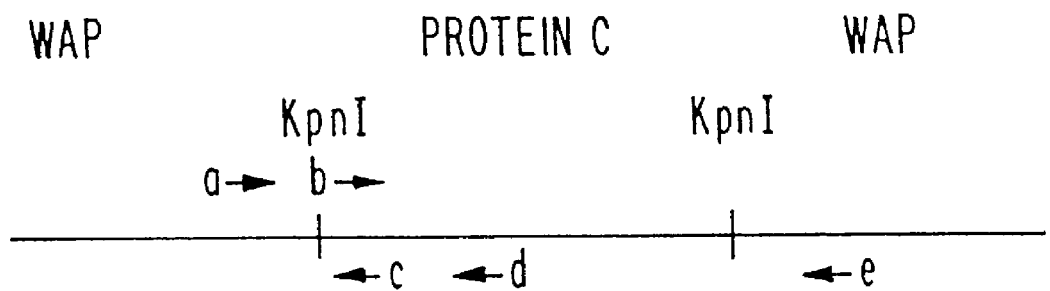
FIG. 2 is a schematic representation of polymerase chain reaction (PCR) primer pairs useful to detect WAP-protein C DNAs in transgenic animals.

Oligonucleotide pairs were used to prime polymerase chain reactions that detected the presence of WAP-protein C constructs in the transgenic animals. These pairs and their extension products are shown schematically in FIG. 2 Oligonucleotide pairs that bridge the region from the WAP sequences 5' of the KpnI site and the endogenous WAP sequences which naturally lie 3' of the KpnI site also provided positive controls in mice.

(3) PCR Reaction Conditions and Product Analysis

PCR reactions were performed using an annealing temperature of 58° C., a denaturation temperature of 94° C., and an extension temperature of 72° C., using 100 ng of oligo primers and 50 ng of (genomic) template DNA per reaction, and cycling through the temperatures 40 times using an automatic temperature cycler (M.J. Research).

PCR reactions were analyzed by running 20% of the reaction products on agarose gels and identifying fragment sizes by comparison with marker DNA fragments.

(4) Results of PCR Analysis of Transgenic Animals

PCR analysis of potentially transgenic mice and pigs which developed from embryos microinjected with WAPpC1 and WAPpC2 constructs are summarized in Table 2. The results show that WAPpC constructs frequently integrated into the embryonic genomes of both mice and pigs. Furthermore, mendelian transmission was observed in 5 of the 16 mice which were tested.

TABLE 2

Whey Acid Protein-Protein C Construct Integration Rates

| Animal | # Tested | # Positive | Integration Rate |
|--------|----------|------------|------------------|
| Mice   | 105      | 30         | 29%              |
| Pigs   | 23       | 5          | 22%              |

Mendelian Transmission in Transgenic Mice
5/16 Tested = 31%

EXAMPLE 5

Preparation of Milk and Whey from Transgenic Animals (A) Mice: Lactating mice were milked an average of 3 times per week. The mice were first separated from their young for approximately 5 hours. They were then anesthetized with 0.4 ml avertin at 2.5% (I.M.), and 0.2 ml oxytocin was then administered at 2.5 IU/ml (I.P.) to permit release of the milk. A milking device consisting of a vacuum pump (2.5 psi) and syringe with an eppendorf tip was used to direct milk into an eppendorf tube. During collection, milk was placed on ice until all samples were obtained.

To prepare whey, milk was diluted 1:1 with TS buffer (0.03M Tris pH 7.4; 0.06 NaCl) and centrifuged in a TLA-100 rotor in a Beckman TL-100 table top ultracentrifuge at 51,000 rpm (89,000×g) for 30 minutes at 4° C. After centrifugation the tubes were put on ice, and the whey was collected with an 18 gauge needle, leaving the casein pellet and upper cream layer in the tube. To remove solids or cream that co-transferred during the initial recovery, the whey obtained from the first centrifugation was subjected to a second spin at 12,000 rpm for 30 minutes at 4° C. in a TMA-4 rotor in a Tomy MTX-150 centrifuge. Following the second spin the tubes were place on ice and the whey was recovered as before.

EXAMPLE 6

Determination by ELISA of Protein C Produced by Transgenic Mammals

An ELISA was used to measure the amount of protein C protein produced by transgenic animals in their milk or whey. Two monoclonal antibodies, 7D7B10 and 12A8, and a polyclonal antiserum were used in the ELISAs, and a variety of other protein C specific antibodies could be employed. The 7D7B10 monoclonal is specific for the $NH_2$ terminus of the light chain of protein C. 12A8 is specific for the reactive site on the heavy chain of protein C.

Microtiter plate wells were coated overnight at 4° C. with 3 $\mu$g/ml of monoclonal antibody in 50 $\mu$l of 0.1M sodium bicarbonate buffer, pH 8.3. The wells were washed once with TET buffer (0.01M Tris pH 7.5; 0.01M EDTA; 0.02% tween-20, pH 7.45) and then blocked with 1% BSA in PBS using 400 $\mu$l per well for 1 hour at 37° C. Plates were again washed with TET buffer (5×) followed by addition of 100 $\mu$l of sample whey or normal whey spiked with human protein C from plasma, to generate a standard curve. After washing 5× with TET buffer, horse radish peroxidase (HRP)-conjugated to rabbit anti-hPC was diluted 1:1000 in 0.1% BSA/TET and 100 $\mu$l was added per well and incubated for 2 hours at room temperature, with shaking at 100 rpm. After again washing 5 times with TET buffer, 100 $\mu$l of orthophenyldiamine (OPD), from a stock solution made by dissolving one tablet of OPD in 20 ml of 0.1M citrate-phosphate buffer (pH 5.0), were added to each well. After 10 minutes at room temperature the reaction was stopped with 1N sulfuric acid. The extent of the reaction was determined by measuring product absorption at 490 nm.

Figure 3:
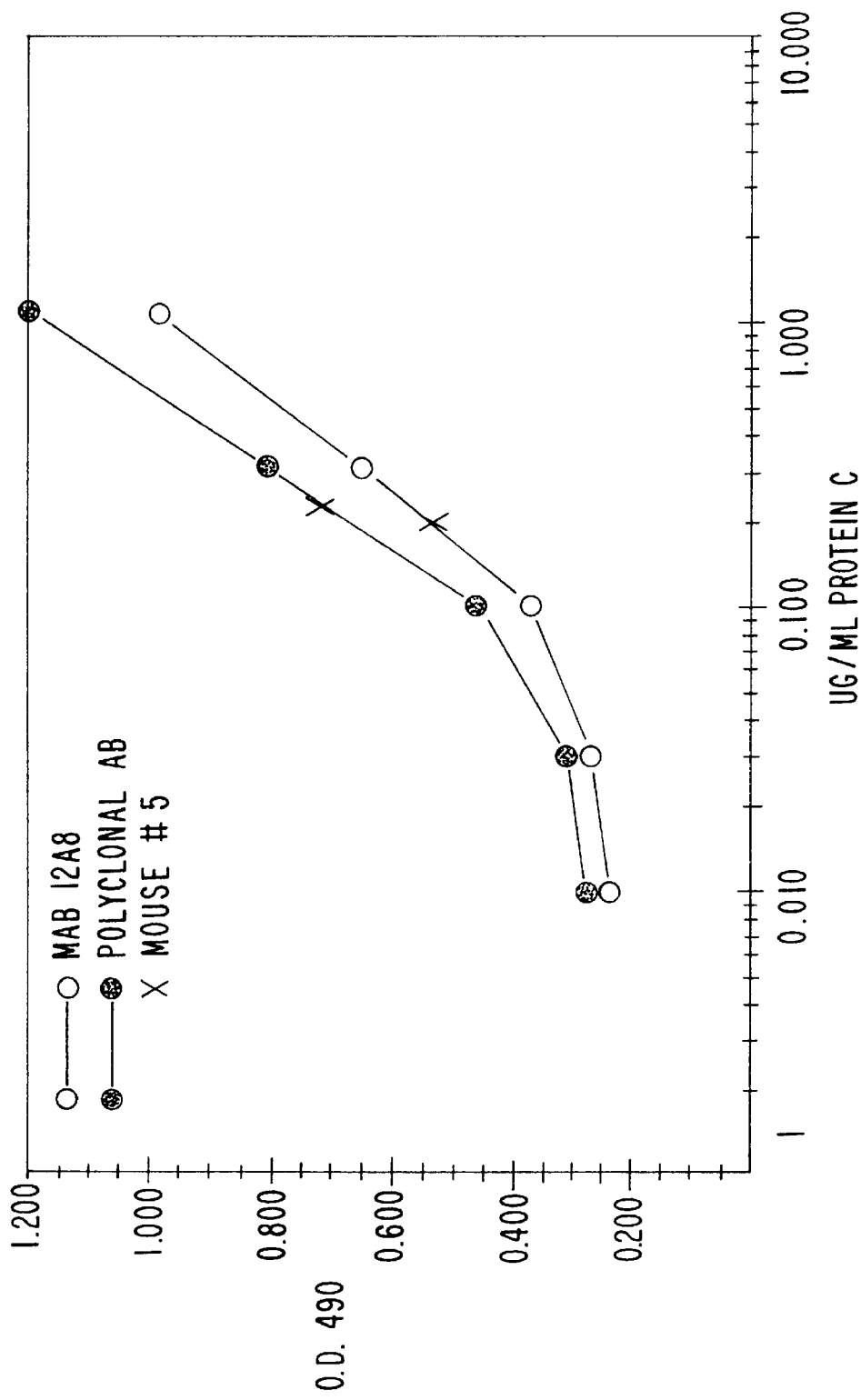
FIG. 3 is a graph that shows the results of an enzyme linked immunosorbent assay (ELISA) of human protein C in milk obtained from a transgenic mouse.

The result of an ELISA analysis of the milk from one transgenic mouse (Mouse No. 5) is shown in FIG. 3. Standard curves were obtained for a monoclonal antibody, 12AB, and a rabbit polyclonal antibody, tittered against human protein C which was obtained by immunoaffinity chromatography over immobilized 7D7B10 antibody. The milk sample, taken from transgenic Mouse No. 5, contained approximately 200 ng/ml protein C.

To assure proper protein C structure as judged by immunocapture by two different monoclonal antibodies, as well as by a polyclonal mixture of antibodies, the samples for several different transgenic mice were screened by ELISAs. Table 2A shows essentially equivalent antigen levels, as judged by three different immunocaptures and detection by ELISA. The majority of mice produced by microinjection of WAPpC1 produced antigen levels in the 1-to-4-μg/ml range.

TABLE 2A hPC ANTIGEN ELISA (NG/ML)

| MOUSE ID-DAY | MONOCLONAL LC-CAPTURE | MONOCLONAL HC-CAPTURE | POLYCLONAL CAPTURE |
|---|---|---|---|
| Y52-15 | 1820 | 3530 | 4100 |
| Y57-15 | 930 | 1150 | 2880 |

The concentration of human protein C in whey obtained from transgenic mice, as well as milk, was also determined in this manner, with equivalent results.

Similar assays were routinely carried out to assay protein C in milk obtained from transgenic animals. Results obtained using the 7D7B10 antibody in light-chain capture ELISAs are compiled in Table 3, which summarizes the concentration of protein C in milk obtained from transgenic mice during the first four lactation periods. Dashes indicate that no test was done. All of the animals provided significant levels of protein C in their milk. Preliminary results also indicate that the second lactation period is sometimes superior to the other periods tested.

TABLE 3 hPC ELISA SCREENING (LIGHT CHAIN CAPTURE)

PC-Ag (μg/ml)

Day of Lactation

| MOUSE ID | 5–6 | 8–9 | 11–12 | 13–15 |
|---|---|---|---|---|
| Y68-L2 | — | 1.05 | — | — |
| Y51-L2 | — | 1.08 | — | 0.56 |
| Y51-L3 | — | 2.80 | 1.30 | 1.79 |
| Y52-L1 | — | 0.55 | 0.65 | — |
| Y52-L2 | — | 1.52 | — | 0.95 |
| Y57-L1 | — | — | 0.52 | 1.35 |
| Y57-L2 | 1.47 | — | 0.98 | — |
| R03-L2 | 1.90 | 2.88 | 3.01 | — |
| R12-L1 | — | 0.60 | — | — |
| R12-L2 | — | 2.98 | 2.48 | 2.40 |

Human protein C in the milk obtained from other species can be measured by the same methods. Thus, protein C from human plasma spiked into pig milk was accurately detected via the above-described ELISA.

EXAMPLE 7

Assay for Protein C Amidolytic Activity using the Chromogenic Substrate S-2366

(1) Microtiter Well Assay

The enzymatic activity of protein C in the milk of transgenic animals was measured directly using a chromogenic assay essentially as described by Odegaard et al., Haemostasis 17: 109 (1989). In this assay microtiter plate wells were coated with the 7D7B10 monoclonal antibody (50 μg/ml) in 50 μl of 0.1M bicarbonate buffer, pH 8.6 at 4° C. overnight. Plates were then rinsed with TET buffer (0.1M Tris; 0.03M EDTA; 0.05% tween-20) and blocked with 400 μl/well 1% BSA in PBS and incubated at room temperature for 1 to 1.5 hours. After rinsing 3 times with TET buffer, 50 μl of whey sample and 50 μl of 0.1M Tris pH 7.5, 0.03M EDTA was added per well and incubated at room temperature for 2 hours. Plates were washed 3 times in TET buffer. The captured human protein C was activated by adding 120 μl of Protac™, a commercial reagent containing a snake-venom enzyme (12 ml distilled water per vial), 30 μl TSP buffer and 0.1% BSA, pH 7.5, per well. After incubation for 6–10 minutes at room temperature, 120 μl S-2366 (Kabi substrate) at 25 mg/10.8 ml Tris pH 7.8 was added to each well and the plates were incubated for 2–8 hours at room temperature, or several days at 4° C. The amount of protein C activity in each sample was determined by measuring formation of the reaction product by absorption at 405 mm.

Results obtained using milk and whey from a transgenic mouse and the pooled milk and whey of several transgenic mice appear in Table 4, which shows the amount and the specific activity of protein C in the samples. Note that the samples were obtained either during the first lactation period, L1, or were obtained from a second and third lactation, L2 and L3. The specific activity of the human protein C obtained from transgenic mice determined in these assays, 205 units (U) per mg, is similar to that of human protein C of similar purity obtained from natural sources. (A "unit" is defined by pooling blood from many individuals and determining activity in 1 ml of the pooled blood.)

TABLE 4

Protac ™-Specific Amidolytic Activity Upon S-2366

|  | U/ml | μg Ag/ml | U/mg |
|---|---|---|---|
| Reconstituted Whey Y52-L1 Pool* | 0.07 | 0.34 | 206 |
| Y52-L1 Milk Pool | 0.23 | 1.12 |  |
| Transgenic Whey Pool** | 1.12 | 0.55 | 205 |
| Transgenic Milk Pool** | 0.43 | 2.10 |  |

*Pooled milk from days 5–15.
**L2 and L3 from mice Y51, Y52, Y57, R03, R12.

(2) Amidolytic activity assay on nitrocellulose

Whey proteins were resolved by electrophoresis through polyacrylamide gels under non-reducing conditions in the presence of SDS. Following electrophoresis proteins were transferred out of the gel and immobilized on a nitrocellulose membrane by electroblotting. SDS was removed from the membrane by thorough washing in 0.05M Tris-Cl, 0.175M NaCl, .25% Triton X-100, pH 8.0, and the membrane was then equilibrated in 0.25M Tris-Cl pH 8.0. Following equilibration the membrane was incubated in Protac C, 0.25 U/ml in distilled water. A 1% agarose indicator gel in 25 mM Tris-Cl pH 8 containing 1 mM chromogenic substrate S-2366 was then placed onto the gel, and the filter and gel overlay were incubated under moist conditions for 30–90 minutes at 37° C. Colored bands generated by protein C activity on the filter were visualized under U.V. light, and photographed.

Figure 8A:
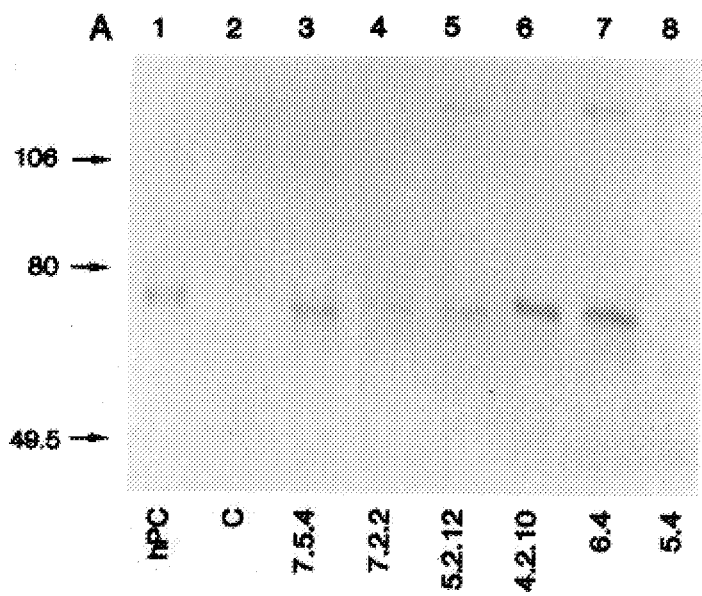
FIG. 8 shows the amidolytic activity in samples of whey from transgenic mice. Panel A shows amidolytic activity of whey proteins resolved by PAGE under native conditions. Panel B shows the proteins detected by anti-hPC antibodies in a western blot of an identical gel, visualized using 4-chloro-1-naphthol. Lanes were loaded with approximately 50 µg of protein. Lane 1 contained purified human protein C. Lane 2 contained a sample form a non-transgenic mouse. Lanes 3 through 8 contained, respectively, samples from transgenic mice 7.5.4, 7.2.2, 5.2.12, 4.2.10, 6.4 and 5.4.
Figure 8B:
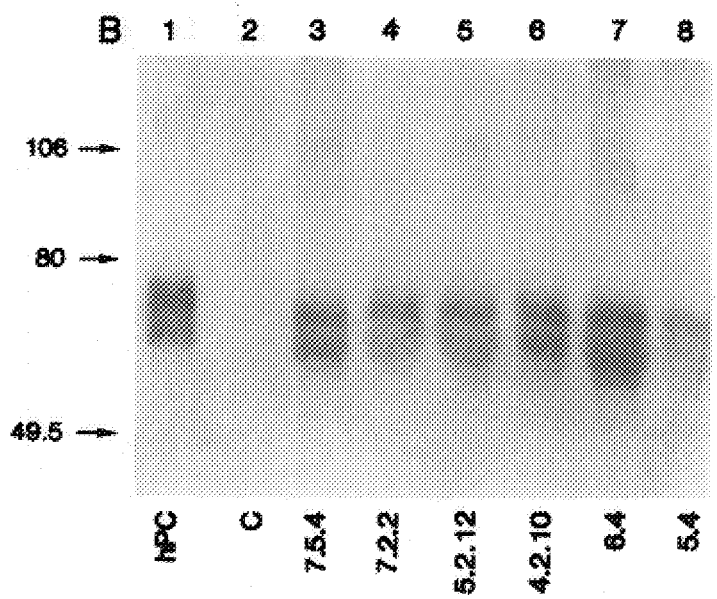

FIG. 8 shows the results obtained by this assay for milk produced by transgenic mice that were stably transformed with a double stranded DNA comprising the 5' 4.2 kb WAP promoter ligated via a linker to the 9.4 kb human genomic protein C fragment. All of these transgenic mice produced amidolytically active protein C in their milk, giving rise in the blots to a strong band and a weak band of amidolytic activity (FIG. 8, panel A). Notably, bands of the same migration were detected in each whey sample when a similar blot was probed with an anti-protein C antibody (FIG. 8, panel B).

EXAMPLE 8

Determination of Protein C Produced in Transgenic Mammals by Activated Partial Thromboplastin Clotting Time Assay The activity of protein C was also measured in a clotting time assay, the activated partial thromboplastin clotting time assay (APTT). In this assay, each well of a plastic Coag-a-mate tray received 90 μl of PC-deficient plasma plus 10 μl of an APC standard or unknown, diluted with Tris/saline/BSA. The tray was then placed on an automated analyzer (APTT mode, 240 second activation). The run was started, which automatically performed the addition of 100 μl of APTT reagent and 100 μl of 0.025M $CaCl_2$. Data obtained using a standard APC preparation was fitted to the equation y=ax+b where y=clotting time and x=APC, which was then used to determine the amount of APC in a sample.

Figure 4:
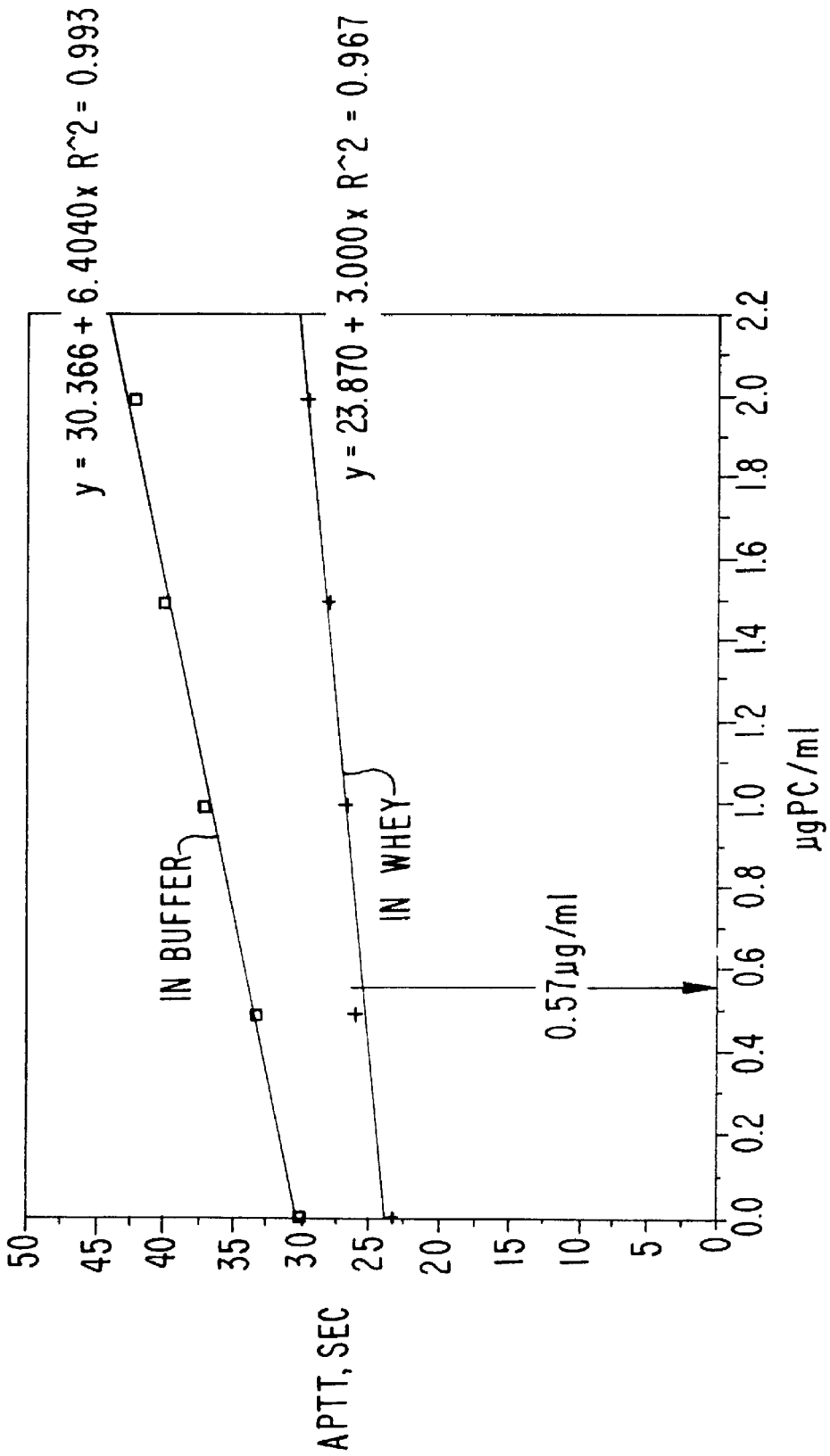
FIG. 4 is a graph that shows the results of an APTT assay to determine human protein C anti-coagulant activity in whey obtained from a transgenic mouse.
Figure 5:
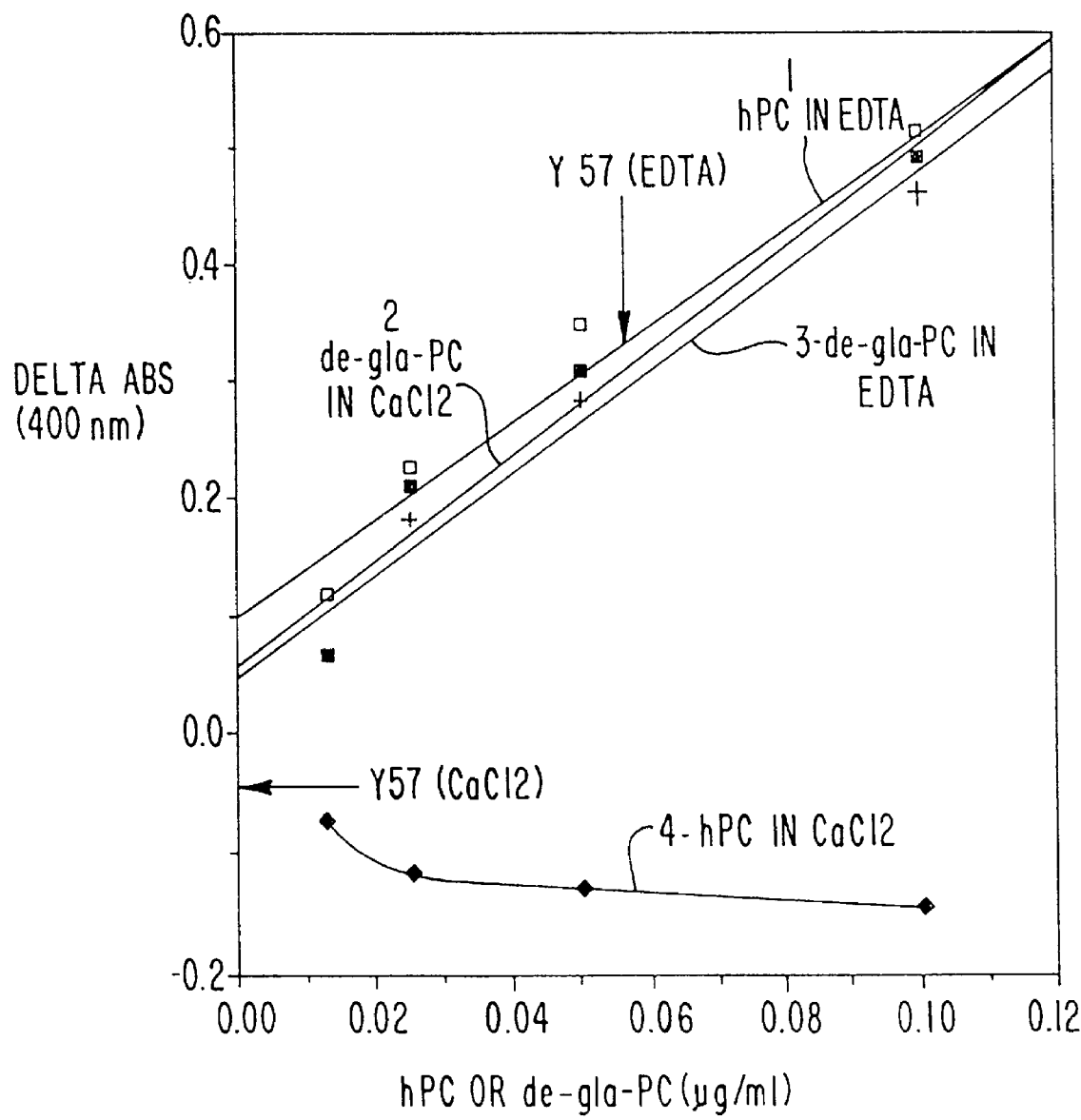
FIG. 5 is a graph that shows the results of $Ca^{2+}$-dependent and $Ca^{2+}$-independent light chain capture ELISAs which demonstrate that the γ-carboxyglutamic acid in human protein C in whey from transgenic mouse Y52 is similar to that in protein C derived from human serum.

The result of an APTT assay of whey pooled from transgenic mice is shown in FIG. 4. The standard curves in the figure correlate the activity determined by the APTT assay with the amount of active human protein C in mouse milk or mouse whey. The activity in the APTT assay of the whey sample obtained from the transgenic mouse corresponded to a concentration of approximately 0.57 μg/ml, interpolated from the standard curve for human protein C in whey. An ELISA (not shown) of the same whey sample detected approximately 0.60 μg/ml of human protein C, as protein. Thus, within the normal range of error of these assays, human protein C produced in transgenic mice is as active as the control human protein C.

EXAMPLE 9

Mapping of Calcium Dependent Conformer by Metal-Dependent Immunoaffinity

Standard ELISAs were run in normal mouse milk whey with varying concentrations of hPC or hPC without Gla regions in the presence of 25 mM EDTA. After capture by 7D7B10, an assay replicating that effected with 25 mM EDTA was treated with several washes of 25 mM $CaCl_2$, and then was followed by the ELISA detection protocol described previously. While de-Gla protein remained bound to the capture antibody in the presence of $CaCl_2$, the PC standard did not remain bound in the presence of added $CaCl_2$. It was observed that whey from the transgenic mouse Y57 behaved in a similar manner to the γ-carboxylated native PC, suggesting that it is also γ-carboxylated like the native molecule.

EXAMPLE 10

Purification of Human Protein C from the Milk of Transgenic Animals (1) Preparation of Whey Samples Milk from several WAPpC1 transgenic mouse lines was pooled, chilled on ice, diluted 6-fold with 50 mM Tris-HCl, 0.15M NaCl pH 7.2 (TBS) (1 ml milk per 5 ml TBS), and centrifuged at 125,000×g for 30 minutes at 4° C. Following centrifugation, the whey was collected and pooled using a pasteur pipet and pooled, being careful not to disturb the fatty overlayer or the casein pellet. Samples were removed from the pool for later assay and then both the samples and the pooled whey were frozen and stored at −90° C. Human protein C in samples was determined by ELISA, as described above.

Individual whey pools were thawed at 2° C.C, combined, and the amount of human protein C (hPC) in the combined pool was determined by ELISA using the 7D7B10 monoclonal antibody (Mab). The combined pool contained approximately 30 μg hPC, determined by this assay, which was within 20% of the total determined by adding determinations of the individual pools.

The combined pool, approximately 150 ml, was dialyzed (14,000 MW cutoff) against 25 mM EDTA-TBS diluted 5-fold with pure water. The dialyzed whey was concentrated 5-fold by lyophilization and subsequent reconstitution with nanopure water, to yield a final buffer concentration equivalent to 25 mM EDTA in TBS, and a 5-fold increase in protein concentration. The concentrated whey contained 930 mg protein, as estimated by optical absorption at 280 nm, at 16 mg/ml.

(2) Immunoaffinity Chromatography

The resin immunosorbent (Affiprep™) used to purify human protein C in the whey of transgenic mice contained 3.3 mg 7D7B10 Mab/ml of Affiprep resin. The 7d7B10 Affiprep resin was assessed by mock immunopurification using 30 μg of plasma derived hPC doped into control (nontransgenic) mouse whey. Approximately the same relative amount of total protein was loaded onto the column (660 mg on a 10 mL Affiprep) and otherwise processed as described below.

Freshly concentrated whey (16 mg/ml, 930 mg total protein, as determined by optical absorption at 280 nm) was batch-loaded onto 13 ml of 7D7B10 Affiprep containing 3.3 mg 7D7B10 Mab/ml resin for 4 hours at 2° C., without addition of carrier protein. The column was fresh and the high total (background) protein loading was thought to be enough to condition the column. The resin was then loaded into a 1 cm diameter column and washed with 25 mM EDTA-TBS until baseline optical density (O.D.) was detected at 280 nm (3 column volumes to obtain <0.0005 O.D.)

The column was then eluted with 25 mM $CaCl_2$ in TBS pH 7.2, followed by 100 mM $CaCl_2$ in TBS, followed by 4M NaCl, followed by 2M Na thiocyanate at 0.5 ml/min. The column was re-equilibrated with 5 column volumes of 25 mM EDTA-TBS, 0.02% sodium azide.

All peak pools were dialyzed in a 100-fold dilution (by nanopure water) of 50 mM imidazole, 0.1M NaCl buffer using a 14,000 MW cutoff dialysis tubing, then lyophilized, then reconstituted to 50 mM imidazole, 0.1 NaCl buffer strength using nanopure water resulting in a 100-fold concentration of protein.

Samples of these eluate pool concentrates were prepared as per the method of Laemmli (1970), applied to a 15 well, 9 cm×2 cm, 4% stacking gel above a 7.5 cm, 7.5% resolving (30%: 2.7% bis) sodium dodecylsulphate polyacrylamide gel and electrophoresed (SDS-PAGE). After electrophoresis, the gel was stained with 1.25% Coomassie Blue dye solution.

The area of the eluate peaks obtained from immunopurification of whey from WAPpC1-transgenic mice was found to be very similar to the mock trial using an equivalent amount of (plasma derived) hPC-doped whey from control mice. Assay of 100-fold concentrated 25 mM $CaCl_2$ eluate product from WAPpC1 transgenics showed 40% yield based upon densitometry of SDS-PAGE stained with Coomassie Blue (yield not determined for mock purification). The total peak areas from mock- and WAPpC1 -whey were approximately the same for all eluate peaks including the 2M Na thiocyanate peak. Approximately 2 μg of hPC antigen (ELISA with immunocapture using 7D7B10 Mab) was detected in the column fallthrough which had been combined with EDTA-TBS wash. Approximately 14 μg of hPC was detected in the 25 mM $Ca^{2+}$ eluate pool, less than 0.1 μg hPC antigen in the 100 mM $Ca^{2+}$ eluate pool, no hPC antigen was detected in the 4M NaCl pool, approximately 10 μg of hPC was detected in the 2M Na thiocynate eluate pool. Thus, 87% of the hPC antigen applied to the column was accounted for in the total antigen recovered from column effluents. A 47% antigen yield was obtained based upon the hPC antigen recovered in the 25 mM Ca$^{2+}$ eluate peak.

The starting whey applied to the column, the 2M sodium thiocyanate eluate, the 25 mM Ca$^{2+}$ eluate product, and a reference hPC derived from plasma by the American Red Cross (Lot #28300277, supplied by Dr. Carolyn Orthner) were analyzed by SDS-PAGE, both reduced and non-reduced. The 2M sodium thiocynate and 25 mM Ca$^{2+}$ eluate pools were concentrated as described above and 4 µg of antigen applied to the gel for each lane. The immunopurified hPC reference was applied to the gel as 4 µg total protein based upon O.D. at 280 nm. Scanning densitometry of this reference hPC indicated that the sample was greater than 99% pure on nonreduced SDS-PAGE, and 71% pure on reduced SDS-PAGE. Subsequent antigen assays performed on the hPC reference material indicated the concentration of the sample to be such that only 2.7 µg of the reference sample was applied to the gel. The 25 mM Ca$^{2+}$ eluate product is greater than 94% pure based upon non-reduced SDS-PAGE and 86% pure based upon reduced SDS-PAGE. The staining intensity of the 25 mM Ca$^{2+}$ eluate lanes is consistent with our previous experience for 4 µg antigen applications. The bands corresponding to reference hPC possessed lighter intensity relative to the 25 mM Ca$^{2+}$ eluate. A slightly split band at approximately 62,000 relative molecular weight (Mr) is seen for both the non-reduced reference hPC and the 25 mM Ca$^{2+}$ eluate. A doublet at about 40,000 Mr and a diffuse single band at 22,000 Mr is seen for both the reduced reference hPC and 25 mM Ca$^{2+}$ eluate. The 22,000 Mr band appearing in the hPC reference is seen to be somewhat more diffuse or heterogeneous than the similar band appearing in the 25 mM Ca$^{2+}$ eluate from the whey of transgenic mice. The sodium thiocyanate peak showed a band in excess of 180,000 Mr in the nonreduced sample and multiple bands at 50,000 Mr and 25,000 Mr in the reduced sample.

The chromatography of the WAPpC1-whey was nearly identical to the mock run using plasma-derived hPC doped into control whey. The total areas and yields of hPC in the 25 mM Ca$^{2+}$ eluates and areas of 2M sodium thiocyanate peaks for both runs were similar and thus the binding characteristics of the 7D7B10 Mab onto transgenic hPC or plasma-derived hPC were similar. This is consistent with the similarity found between plasma-derived and transgenic hPC Ca$^{2+}$—dependent conformers as judged by ELISA assays using the 7D7B10 Mab to immunocapture from whey. The primary structure as judged by SDS-PAGE appears to be similar, with the amount of α-form and β-form heavy chain being essentially the same for plasma-derived and transgenic hPC; the transgenic having 68% α-form and 32% µ-form while the plasma-derived material possessed 69% a-form and 31% β-form. The light chains were also similar in size for both reference and transgenic hPC. Previous experience with SDS-PAGE using Coomassie Blue staining of hPC has shown linearity for both chains over the range of 2–5 µg hPC applied to the gel. Thus, much of the elements of post-translational, proteolytic processing appears to have occurred properly in the mammary tissue.

The purity of these runs also demonstrates the satisfactory utility of the immunopurification procedure developed for the murine system. It is believed that the tight binding of the hPC antigen found by ELISA in the 2M thiocyanate peak of the whey from transgenic mice (assay not done for mock run) is typical of yields found for fresh immunosorbents and not due to an aberrant hPC structure. The total background protein did not seem to condition the column and thus the interaction is thought to be specific with the 7D7B10 Mab. Overall, this two step procedure results in a minimum purification factor of 27,000 for the hPC recovered from mouse milk. A large-scale purification process could employ a citrate or EDTA precipitation coupled with low speed centrifugation in place of the ultracentrifugation step used for mouse milk.

Both amidolytic and anti-coagulant assays were performed upon immunopurified milk from transgenic mice. Within the sensitivity of these assays, the amidolytic and anti-coagulant activity was the same as plasma-derived immunopurified protein C. For both types of assays, the specific activity was greater than 270 U/mg.

EXAMPLE 11

Highly Efficient Expression of Active Protein C in Transgenic Mammals using a Long Mouse Whey Acid Protein Promoter Fragment and a Human Genomic Protein C Fragment (A) DNA Constructs The 5' 4.2 kb Sau3A-Kpn1 promoter fragment of the mouse whey acidic protein promoter was cloned by standard techniques. The 9.4 kb genomic fragment of human protein C beginning 21 basepairs upstream of the "A" in the protein C start codon and ending at the NheI site in the 3' end of the protein C gene also was cloned by standard techniques. The 4.2 kb promoter fragment and the 9.4 kb protein C fragment were joined using a SalI linker, as shown in FIG. 6.

(B) Production of Transgenic Animals

DNA was prepared and injected into mouse and pig embryos as described hereinabove. Animals were tested for integration of the DNA by PCR, also as described above. Stable integration of the construct was detected in both mice and pigs.

(C) Protein C in the Milk of Transgenic Mice.

The mice were reared to maturity, crossed and milk was obtained from lactating females.

Figure 7A:
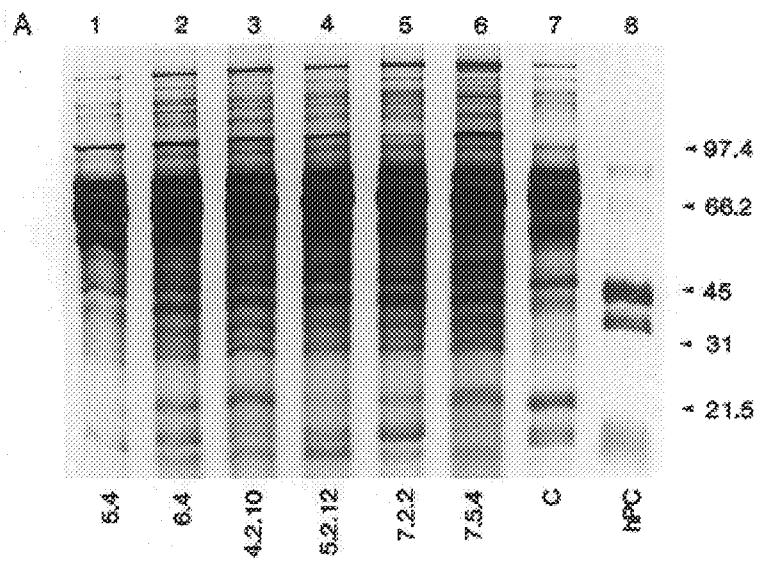
FIG. 7 is a photograph showing the results of western analyses of human protein C production in the milk of transgenic animals. Panel A shows the proteins in whey samples resolved by PAGE under reducing conditions and visualized by silver staining. Panel B shows the proteins detected by anti-human protein C antibodies in a western blot of an identical gel, visualized by chemiluminescence. Lanes were loaded with approximately 5 µg of protein. Lanes 1 through 6 contained, respectively, samples from transgenic mice 5.4, 6.4, 4.2.10, 5.2.12, 7.2.2 and 7.5.4. Lane 7 contained a sample from a non-transgenic mouse. Lane 8 contained purified human protein C. "SC"—single chain hPC, "HC"—heavy chain forms of hPC, "LC"—light chain hPC.
Figure 7B:
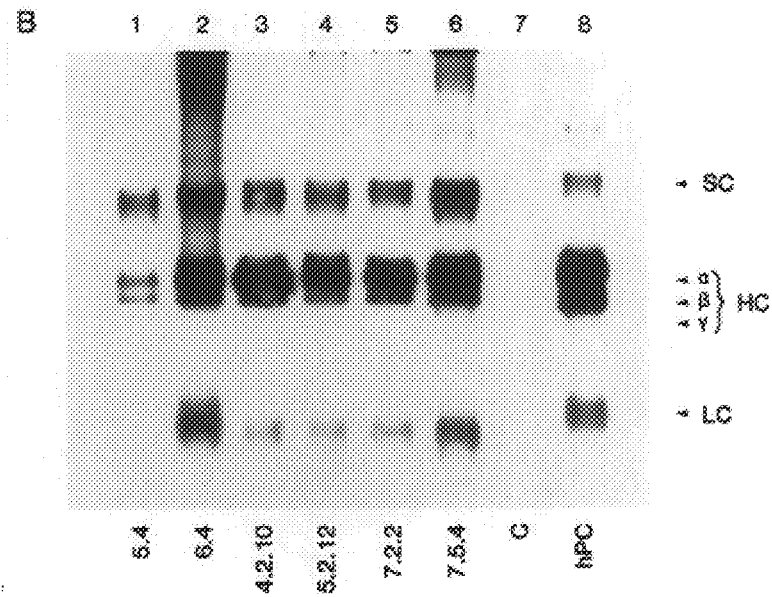

FIG. 7 depicts SDS-PAGE and western blot analysis of whey from six transgenic mice. As shown in panel A, transgenic mouse whey (lanes 1–6) and normal mouse whey (lane 7) gave rise to substantially the same silver stain pattern of bands after SDS-PAGE. As shown panel B, human protein C readily was detected in the transgenic mice whey (lanes 1–6), but not in normal mouse whey (7), when the samples were blotted onto nitrocellulose, probed with an anti-human protein C antibody, and visualized by chemiluminescence. The pattern of bands detected by the anti-human protein C antibody in the transgenic mouse whey was very similar to the pattern of bands detected in purified human protein C (lane 8).

As shown in FIG. 8, protein C activity readily could be detected in transgenic mouse whey. Panel B in the figure shows the pattern of human protein C in mouse whey samples resolved by SDS-PAGE under non-reducing conditions. Protein C was visualized by blotting onto nitrocellulose, probing the filter with an anti-human protein C antibody and detecting antibody binding by a secondary-antibody-enzyme conjugate and the chromogenic substrate 4-chloro-l-naphthol. Protein C reactive bands were substantially the same in transgenic mice (lanes 3–8) and purified human protein C (lane 1), and were absent from normal mouse whey (lane 2).

Amidolytic activity in the samples is shown in Panel A. An agarose gel overlay containing chromogenic substrate revealed enzyme activity in whey from each transgenic mouse (lanes 3–8) and in purified human protein C (lane 1), but not in normal mouse whey (lane 2).

The amounts of human protein C produced by the transgenic mice in their milk also was determined. Table 5 shows the amounts of human protein C detected in the milk of six transgenic mice, as determined by 12A8 monoclonal ELISA and by sheep anti-human protein C polyclonal ELISA. The table also shows protein C amidolytic activity in whey from the same samples. The ELISAs and the amidolytic activity assay were performed as described hereinabove.

As shown in the Table, protein C concentrations in the transgenic mice by monoclonal ELISA ranged from approximately 0.05 mg/ml to approximately 1.69 mg/ml. The concentration of protein C in the milk of these mice was at least 40 fold more than the concentration of protein C observed in other transgenic mice, such as those noted in Table 2A, as set forth hereinabove.

Concentrations measured by polyclonal ELISA ranged from 0.14 to 4 mg/ml, exceeding even more dramatically the concentrations attained with the 2.4 kb 5' WAP promoter, the highest of which, as set forth in Table 2A, was 0.0041 mg/ml.

In addition, whey samples from the transgenic mice were assayed for amidolytic activity and the results were compared with amidolytic activity of protein C in plasma. Amidolytic activity in the samples is shown in Table 5, expressed as the per cent of protein C activity in plasma. The concentration of protein C in the whey samples was adjusted to equal the concentration in the normal plasma control.

The high concentration of protein C allowed the amidolytic activity to be assayed directly in whey. This contrasted sharply with the necessity to use a capture method to concentrate protein C prior to amidolytic activity of whey samples from mice transgenic for the 2.4 kb WAP promoter fragment.

The amidolytic activity of protein C in the whey sample was also compared with the activity of purified human protein C diluted in whey. At comparable concentrations of protein C, amidolytic activity in transgenic mouse whey was nearly the same as that of human protein C.

TABLE 5

Detection of human protein C in the milk of transgenic mice having the 5' 4.2 kb WAP-promoter-9.4 kb human genomic protein C construct stably integrated in their genomes

| MOUSE NUMBER | TRANS-GENE COPY NUMBER | PC ANTIGEN BY 12A8-MAB ELISA (mg/ml) | PC ANTIGEN BY POLY-CLONAL ELISA (mg/ml) | AMIDOLYTIC ACTIVITY IN WHEY (%N-PLASMA) |
|---|---|---|---|---|
| 5.4 | 14 | 0.05 + −0.01 | 0.14 + −0.01 | N.D. |
| 6.4 | 10 | 1.00 + −0.03 | 2.94 + −0.09 | 56.2 |
| 4.2.10 | 10 | 1.69 + −0.09 | 3.98 + −0.09 | 54.8 |
| 5.2.12 | 20 | 0.96 + −0.09 | 2.50 + −0.10 | 54.9 |
| 7.2.2 | 2 | 0.33 + −0.03 | 0.89 + −0.14 | N.D. |
| 7.5.4 | 30 | 0.96 + −0.04 | 1.99 + −0.33 | 18.8 |

Finally, some of the transgenic mice were sacrificed and examined to determine the tissue specificity of expression of human protein C. RNA blots and immuno in situ histological examination showed that at least 99% of the protein C expression occurred in the mammary glands in these animals. These results contrast with the results achieved using whey acidic protein promoter constructs that contained only the 2.4 kb promoter fragment. Constructs using this promoter to drive protein expression in transgenic mice engendered expression that differed from the normal pattern of whey acidic protein expression during development and in adult tissues. In fact, this was true for the whey acidic protein itself. Thus, in addition to providing high levels of expression of a protein, the 4.2 kb 5' WAP promoter fragment also provides greater tissue specificity of expression in the adult mouse.

(D) Purification of Protein C from Transgenic Mouse Whey

Human protein C was partially purified from transgenic mouse whey by immunoaffinity chromatography using the 12A8 monoclonal antibody immobilized on a Sepharose support. Bound protein C was eluted in 0.1M glycine, 0.02M histidine, 0.15M NaCl pH 10. Transgenic protein C purified in this manner revealed essentially the same banding pattern upon SDS-AAGE as a standard preparation of purified human protein C.

What we claim is:

1. A transgenic non-human mammal containing a DNA sequence stably integrated in its genome, wherein said exogenous DNA sequence comprises the 5' 4.2 kb Sau3A-Kpn1 promoter of the mouse whey acidic protein gene, operably linked to a DNA sequence encoding heterologous protein C and a signal peptide, wherein said whey acidic protein promoter is specifically active in mammary cells and said signal peptide is effective in directing the secretion of said protein C into the milk of said transgenic mammal, wherein the activated form of said secreted protein C has an enzymatic activity of at least 50% as plasma-derived protein C, and wherein said transgenic mammal is selected from the group consisting of mice, rats, rabbits, pigs, sheep, goats and cows.

2. The transgenic non-human mammal of claim 1, wherein said protein C is human protein C, and wherein said DNA sequence encoding protein C further comprises regulatory elements located in the non-coding regions of the human protein C gene, wherein said regulatory elements are the AUG start codon, donor and acceptor splice signals, the secretion peptide, translation termination signal, transcription termination signal, and polvadenylation signal.

3. The transgenic non-human mammal of claim 1, wherein said DNA sequence encoding human protein C comprises the human protein C gene from 21 basepairs upstream of the protein C start condon to the NehI site in the 3' end of the protein C gene.

4. The transgenic non-human mammal of claim 1, wherein said exogenous DNA sequence comprises a DNA sequence comprising the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene.

5. A process for the production of heterologous protein C, comprising the steps of:

(A) providing a non-human transgenic mammal whose genome comprises a stably integrated DNA sequence comprising the 5' 4.2 kb Sau3A-Kpn1 promoter of the mouse whey acidic protein gene, operably linked to a DNA sequence encoding a heterologous protein C and a signal peptide, said promoter being specifically active in mammary cells and said signal peptide being effective in directing the secretion of said protein C into the milk of said transgenic mammal, and wherein said transgenic mammal is selected from the group consisting of mice, rats, rabbits, pigs, sheep, goats and cows;

(B) producing milk from said transgenic mammal, wherein said milk contains said secreted protein C, and wherein the activated form of said protein C has an enzymatic activity of at least 50% as plasma-derived protein C;

(C) collecting said milk; and (D) isolating said protein C from said milk.

6. The process of claim 5, wherein said protein C is human protein C, and wherein said DNA sequence encoding protein C further comprises regulatory elements located in the non-coding regions of the human protein C gene, wherein said regulatory elements are the AUG start codon, donor and acceptor splice signals, the secretion peptide, translation termination signal, transcription termination signal, and polyadenylation signal.

7. The process of claim 5, wherein said DNA sequence encoding human protein C comprises the human protein C gene from 21 basepairs upstream of the protein C start codon to the NheI site in the 3' end of the protein C gene.

8. The process of claim 5, wherein said DNA comprises a DNA sequence comprising the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene.

9. A process for producing non-human transgenic mammals, comprising the steps of (A) providing a mixture containing a double-stranded DNA; (B) subjecting said mixture to anion-exchange high performance liquid chromatography to obtain purified double-stranded DNA; and thereafter (C) microinjecting an aqueous buffer solution containing said purified double-stranded DNA into an animal embryo, wherein said double-stranded DNA is selected from the group consisting of a double-stranded DNA comprising the 5' 4.2 kb Sau3A-Kpn1 promoter fragment of the mouse whey acidic protein promoter, a double-stranded DNA comprising a fragment of the human protein C gene beginning 21 basepairs upstream of the protein C start codon and ending at the NheI site in the 3' end of the protein C gene, and a double-stranded DNA comprising a DNA sequence comprising the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene, wherein the activated form of protein C encoded by said double-stranded DNA has an enzymatic activity of at least 50% as plasma-derived protein C, and wherein said transgenic mammal is selected from the group consisting of mice, rats, rabbits, pigs, sheep, goats and cows.

10. A transgenic non-human mammal containing a DNA sequence stably integrated in its genome, wherein said DNA sequence comprises the 5' 4.2 kb Sau3A-Kpn1 promoter fragment of the mouse whey acidic protein promoter, operably linked to a DNA sequence encoding a heterologous polypeptide whereby said polypeptide is expressed specifically in mammary cells of said transgenic mammal and said polypeptide comprises a signal peptide, said signal peptide being effective in directing the secretion of said polypeptide into the milk of said mammal.

11. The transgenic non-human mammal of claim 10, wherein said transgenic non-human mammal is selected from the group consisting of mice, rats, rabbits, pigs, sheep, goats and cows.

12. The mammal of claim 11, wherein said transgenic non-human mammal is sheep.

13. The mammal of claim 11, wherein said transgenic non-human mammal is a goat.

14. The mammal of claim 11, wherein said transgenic non-human mammal is a cow.

15. A process for the production of a heterologous polypeptide in the milk of a transgenic non-human mammal, comprising the steps of:

(A) providing a non-human transgenic mammal whose genome comprises a stably integrated DNA sequence comprising the 5' 4.2 kb Sau3A-Kpn1 promoter of the mouse whey acidic protein gene, operably linked to a DNA sequence encoding a heterologous polypeptide and a signal peptide, said promoter being specifically active in mammary cells and said signal peptide being effective in directing the secretion of said polypeptide into the milk of said transgenic mammal;

(B) producing milk from said transgenic mammal, wherein said milk contains said polypeptide;

(C) collecting said milk; and (D) isolating said polypeptide from said milk.

16. The process of claim 15, wherein said transgenic non-human mammal is selected from the group consisting of mice, rats, rabbits, pigs, sheep, goats and cows.

17. The process of claim 16, wherein said transgenic non-human mammal is a sheep.

18. The process of claim 16, wherein said transgenic non-human mammal is a goat.

19. The process of claim 16, wherein said transgenic non-human mammal is a cow.

20. An isolated DNA molecule which regulates the expression of a heterologous gene, wherein said DNA molecule consists of the 5' 4.2 kb Sau3A-Kpn1 promoter of the mouse whey acidic protein gene.

* * * * *

UNITED STATES PATENT AND TRADEMARK OFFICE
CERTIFICATE OF CORRECTION

PATENT NO.    : 5,831,141
DATED         : November 3, 1998
INVENTOR(S)   : Henryk Lubon et al.

It is certified that error appears in the above-identified patent and that said Letters Patent is hereby corrected as shown below:

<u>Title page,</u>
Item [75], the correct listing of inventors should read as follows:

-- [75] Inventors:  Henryk Lubon, Rockville, Md.; William N. Drohan, Springfield, Va.; Lothar Hennighausen, Chevy Chase, MD.; William H. Velander, Blacksburg, Va. --

Signed and Sealed this

Third Day of December, 2002

JAMES E. ROGAN
*Director of the United States Patent and Trademark Office*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGTACGTCGA  CACAGGTGCC  AGTGCCTCCA  GAATGTGGCA  GCTCACAAGC  CTCCTGCTGT         60

TCGTGGCCA                                                                     69
```